United States Patent [19]

Nikaido et al.

[11] Patent Number: 5,874,613
[45] Date of Patent: Feb. 23, 1999

[54] 3-(3-CHLOROPHENYL) SERINE

[75] Inventors: Teruyuki Nikaido; Naoki Kawada, both of Tsukuba; Takeshi Hamatani, Arai; Yoichiro Ueda, Tsukuba, all of Japan

[73] Assignee: Daicel Chemical Industries, Ltd., Sakai, Japan

[21] Appl. No.: 839,215

[22] Filed: Apr. 22, 1997

Related U.S. Application Data

[62] Division of Ser. No. 696,844, Aug. 29, 1996, Pat. No. 5,731,175.

[30] Foreign Application Priority Data

| Mar. 3, 1994 | [JP] | Japan | 6-33912 |
| Mar. 3, 1994 | [JP] | Japan | 6-33916 |
| Oct. 17, 1994 | [JP] | Japan | 6-250759 |

[51] Int. Cl.⁶ ............................................ C07C 229/00
[52] U.S. Cl. ............................................ 562/445
[58] Field of Search ........................................ 562/445

[56] References Cited

U.S. PATENT DOCUMENTS

| 2,986,578 | 5/1961 | Kaneko | 562/445 |
| 3,010,992 | 11/1961 | Brathge | 562/445 |
| 3,871,958 | 3/1975 | Nakazawa | 195/29 |

FOREIGN PATENT DOCUMENTS

| Shu 54-12554 | 5/1979 | Japan . |
| 60-190749 | 9/1985 | Japan . |
| 63-214188 | 9/1988 | Japan . |
| 695741 | 8/1953 | United Kingdom | 562/445 |
| 2146020 | 4/1985 | United Kingdom | 562/445 |

OTHER PUBLICATIONS

Caroline Vergne, "Synthesis of Four Atropdiastereoisomers of C–O–D–O–E Ring of Vancomycin By Sequential Cycloetherifications", Tetrahedron Letters, vol. 38, No. 8, pp. 1403–1406, Feb. 24, 1997.

Fiziol. Akt. Veschestva (1992) 22: 43–45.

Richard J. Ulevitch et al., "Studies of the Reactions of Substituted D, L–Erythro–βPhenylserines with Lamb Liver Serine Hydroxymethylase. Effects of Substituents upon the Dealdolization Step", Biochemistry, vol. 16, No. 24, pp. 5355–5363, (1977).

*Primary Examiner*—Michael L. Shippen
*Attorney, Agent, or Firm*—Oblon, Spivak, McClelland, Maier & Neustadt, P.C.

[57] ABSTRACT

Tyrosine decarboxylase, or microorganisms of the genuses Enterococcus, Lactobacillus, Providencia, Fusarium, and Gibberella were reacted with a mixture of the enantiomers of threo-3-phenylserine or its halogen substitution products to produce (R)-2-amino-1-phenylethanol or its halogen substitution products. At the same time, one of the enantiomers of threo-3-phenylserine or its halogen substitution products were selectively left, and optically active threo-3-phenylserine or its halogen substitution products were produced. In addition, a novel material of 3-(3-chlorophenyl) serine, which is a substrate of the reaction in the present invention, was produced. (R)-2-amino-1-phenylethanol or its halogen substitution products, and optically active threo-3-phenylserine or its halogen substitution products can economically be produced on an industrial scale.

3 Claims, No Drawings

3-(3-CHLOROPHENYL) SERINE

This is a Division of application Ser. No. 08/696,844 filed on Aug. 29, 1996, U.S. Pat. No. 5,731,175, which was filed as International Application No. PCT/JP95/00337 on Mar. 2, 1995.

FIELD OF THE INVENTION

The present invention relates to a method of producing (R)-2-amino-1-phenylethanol or its halogen substitution products, and optically active phenylserine and its halogen substitution products, which are represented by Formula (2), using an enzyme or microorganism. The present invention also relates to a chemical compound 3-(3-chlorophenyl) serine, which is a substrate of the reaction of the enzyme or microorganism. (R)-2-amino-1-phenylethanol and its halogen substitution products, represented by Formula (2), are industrially useful as raw materials of medical or agricultural chemicals, especially anti-obesity drugs. The optically active phenylserine and its halogen substitution products are useful as raw materials for medicines, especially antibiotics.

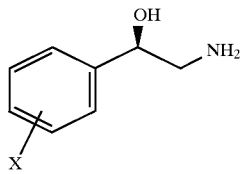

Formula (2)

X is H, F, Cl, Br, or I, and may be located at any of the ortho, meta, and para positions.

BACKGROUND OF THE INVENTION

There have conventionally been several methods for producing (R)-2-amino-1-phenylethanol or its halogen substitution products, represented by Formula (2). The following methods for producing optically active 2-amino-1-phenylethanol or its halogen substitution products are known:

(1) optical resolution by lipase (*J. Chem. Soc. Perkin Trans.*, 1, 1759–1762 (1992));

(2) preparing (R)-mandelonitrile by (R)-oxynitrilase, and then reducing it using LiAlH$_4$ (*Synthesis*, (7), 575–578 (1990));

(3) asymmetrically reducing α-chloroacetophenon using bakers' yeast, and then aminating the product (*Indian J. Chem.*, Sect. B, 31B(12), 821–823 (1992));

(4) aminating an optically active styrene oxide (Japanese Patent Laid-Open Publication No. Sho 61-85197);

(5) selectively crystallizing the (R)-form of a 3-amino benzoate (*Nippon Kagaku Kaishi* (5), 910–913 (1985));

(6) asymmetrically reducing benzoyl cyanide with the presence of alpine borane to obtain the R form (*J. Org. Chem.*, 50, 3237–3239 (1985));

(7) asymmetrically reducing in the presence of a catalyst of binaphthyl phosphine substituting an alkali metal sulfonate (Japanese Patent Laid-Open Publication No. Hei 5-170780).

The following method for producing (R)-2-amino-1-(3-chlorophenyl)ethanol is the only method known:

(8) mixing a solution of N-(t-butoxycarbonyl)-D-alanine and a solution of racemic 2-amino-1-(3-chlorophenyl) ethanol, forming a salt of diasteroisomers, and then optically resolving the salt by means of preferentially crystallizing a salt of (R)-2-amino-1-(3-chlorophenyl) ethanol and N-(t-butoxycarbonyl)-D-alanine (European Patent Laid-Open Publication No. 294995).

The following methods for producing optically active phenylserine and its halogen substitution products are known:

(9) performing aldol condensation of 2-formyl-3-hydroxy [2.2]para-cyclophane (*Angew. Chem.*, 106 (1), 106–108 1994));

(10) performing aldol condensation using aldolase, or conversely treating a racemate with aldolase and leaving an enantiomer (Japanese Patent Laid-Open Publications No. Hei 6-165693 and No. Hei 6-125786; Japanese Patent Publication No. Sho 52-46313; *Can. J. Chem.*, 72 (1), 114–117 (1994));

(11) using an artificial enzyme comprising a lipid having (S)-binaphthol and (S)-alanine, a pyridoxal derivative, and Cu(II) (*Chem. Lett.*, (1), 55–58 (1994));

(12) optically resolving an N-phenylacetylated derivative using penicillin acylase (*Bioorg. Khim.*, 19 (4), 478–483 (1993));

(13) using serine hydroxymethyl transferase (*Tetrahedron*, 48(12), 2507–2514 (1992));

(14) brominating an N-phthaloyl-α-amino acid ester using N-bromosuccinimide, and then reacting with AgNO$_3$ (*Tetrahedron Lett.*, 31 (48), 7059–7062 (1990));

(15) condensing an isocyanocarboxylic acid and an aldehyde in the presence of an optically active ferrocene and a gold complex to form an optically active oxazoline, and then hydrolyzing the optically active oxazoline (Japanese Patent Laid-Open Publication No. Sho 63-60977);

(16) performing aldol condensation of an aldehyde and a Ni(II) complex of a Schiff base derived from (S)-o-[N-(N-benzylprolyl)amino]benzophenone and glycine (*J. Chem. Soc. Perkin Trans.* 1 (24), 3143–3155 (1993)).

With regard to 3-(3-chlorophenyl) serine, a substrate of the reaction used in the present invention, its erythro form has been reported (R. J. Ulevitch and R. G. Kallen, *Biochemistry*, 16 (24), 5355–5363 (1977)), but no detailed synthesizing method is described.

The conventional methods for producing (R)-2-amino-1-phenylethanol or its halogen substitution products, have the following problems:

In Method (1), the enzyme used is expensive, the separation of the product is not easy, and the yield is not high.

Also, in Method (2), the enzyme used is expensive, and is required at a high concentration of 10,000 U/l.

In Method (3), both reaction yield and substrate concentration are low.

In Method (4), the amount of optically active ethylene oxide produced by the microbial reaction is very small, resulting in high cost.

In Method (5), the solubility of the benzoate is low, and the amount of crystals obtained in one batch is small, which is not economical.

In Method (6), the alpine borane is expensive, and its optical purity is not sufficiently high.

In Method (7), the binaphthyl phosphine catalyst is very expensive.

In Method (8), very expensive N-Boc-D-alanine requires an efficient recovering method, which precludes it from industrial use.

As described above, the conventional methods cannot realize industrial and economical production of (R)-2-amino-1-phenylethanol and its halogen substitution products, represented by Formula (2). Therefore, there is a desire to develop a method for producing (R)-2-amino-1-phenylethanol and its halogen substitution products, which can be industrially employed.

The conventional methods for producing optically active phenylserine and its halogen substitution products, have the following problems:

In Methods (9), (11), (15), and (16), a large amount of an optically active catalyst needs to be synthesized. Difficulty and high cost accompany this synthesis. Therefore, these methods are not practical. The configuration of two successive asymmetric centers cannot be completely controlled. Consequently, the product must be further purified by other means such as column chromatography. In addition, this reaction occasionally requires a very low temperature of −80° C.

In Methods (10) and (13), the concentration of the obtained product is low, and an aldehyde used may cause the inactivation of the enzyme. In these synthesizing reactions, the configuration at the 3 position cannot be controlled.

In Method (12), the enzyme itself is expensive.

In Method (14), the ratio of (2S, 3R)-form to (2S, 3S)-form is 5:1. The stereoselectivity is not satisfactory, and furthermore the reaction requires multiple steps.

As shown above, the conventional methods do not enable industrial economical production of optically active phenylserine and its halogen substitution products.

Tyrosine decarboxylase (EC 4.1.1.25) exists in microorganisms, and is known as an enzyme which catalyzes the reaction converting L-tyrosine into tyramine. Pyridoxal-5'-phosphate is a coenzyme of this enzyme (E. A. Boeker and E. E. Snell, "The Enzyme" Vol. 6, pp. 217–253, Academic Press, New York (1972)). The activity of tyrosine carboxylase is observed in the genuses Latobacillus, Pseudomonas, and Enterococcus. Especially, *Enterococcus faecalis* is widely known to have high activity. Several studies of the substrate specificity of these enzymes have been reported. In most of them, substrates in which the hydrogen atom of the phenyl group in tyrosine molecules is replaced at the para position, or at the para and meta positions, are investigated (for example, R. Ferrini and A. Glasser, *Biochem. Pharmacol.,* 13, 798–801 (1964)). No substrate in which the hydrogen atom is replaced with a hydroxyl group at the β position has been investigated at all. Japanese Patent Publication No. Sho 52-31428 discloses that an aromatic amino acid decarboxylase derived from microorganisms of the genus Micrococcus, slightly acts on DL-3-phenylserine. However, neither the optical purity nor accurate concentration of the product is described. A microorganism of the genus Fusarium has been reported to have the activity of phenylalanine decarboxylase (M. Ferencik and K. Ladzianska, *Folia Microbiology,* 13, 414–418 (1968)). However, it has not been clarified what species has the activity of phenylalanine decarboxylase, nor is it described whether the microorganism acts on a substrate provided by the present invention. No investigations have been reported as to whether a microorganism of the genus Gibberella has the activity of an amino acid decarboxylase.

Thus, the following matters have not been known: Tyrosine decarboxylase, or microorganisms of the genuses Enterococcus, Lactobacillus, Providencia, Fusarium, and Gibberella act on enantiomer mixtures of threo-3-phenylserine or its halogen substitution products to produce (R)-2-amino-1-phenylethanol or its halogen substitution products. At the same time, one of the enantiomers of threo-3-phenylserine or its halogen substitution products is selectively left to produce optically active threo-3-phenylserine or its halogen substitution products.

DISCLOSURE OF THE INVENTION

In order to solve the problems mentioned above, the inventors focussed on facilitating substrate synthesis, economization, stereoselectivity of a reaction by microorganisms, and stereoselective decarboxylating reaction by enzymes, and carried out extensive investigations. The inventors found that tyrosine decarboxylase, or microorganisms of the genuses Enterococcus, Lactobacillus, Providencia, Fusarium and Gibberella acted on threo-3-phenylserine or its halogen substitution products, represented by Formula (1), and produced (R)-2-amino-1-phenylethanol or its halogen substitution products, represented by Formula (2) with an optical purity of almost 100%. They additionally found that one of the enantiomers of threo-3-phenylserine or its halogen substitution products was simultaneously selectively left to produce optically active threo-3-phenylserine or its halogen substitution products, and then accomplished the present invention.

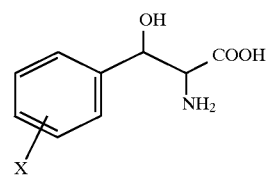

Formula (1)

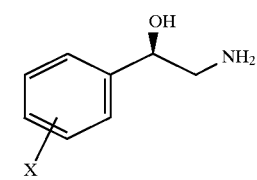

Formula (2)

X is H, F, Cl, Br, or I, and may be located at any of the ortho, meta, and para positions.

The present invention provides a method for producing (R)-2-amino-1-phenylethanol or its halogen substitution products, optically active phenylserine and its halogen substitution products, and a novel chemical compound 3-(3-chlorophenyl)serine. According to the present invention, a mixture of enantiomers of threo-3-phenylserine or its halogen substitution products, which are represented by Formula (1), is treated with tyrosine decarboxylase, or microorganisms of the genuses Enterococcus, Lactobacillus, Providencia, Fusarium, and Gibberella, which are capable of stereospecifically decarboxylating the above compounds to produce (R)-2-amino-1-phenylethanol or its halogen substitution products, which are represented by Formula (2), and collected. Simultaneously, one of the enantiomers of threo-3-phenylserine or its halogen substitution products is selectively left, and optically active threo-3-phenylserine or its halogen substitution products are collected.

Tyrosine decarboxylase used in the present invention may be derived from any source. Tyrosine decarboxylase derived from a microorganism, such as *Enterococcus faecalis* or *Enterococcus hirae,* is easily obtained, being prefer-ably employed. (*Streptococcus faecalis* is the former name of *Enterococcus faecalis.* The tyrosine decarboxylase from *Streptococcus faecalis* is actually an enzyme derived from a microorganism of the genus Enterococcus. In the classification revised in 1981, the genus Enterococcus has been separated from the genus Streptococcus. According to "Bergey's Manual of Systematic Bacteriology (1986)", the former *Streptococcus faecalis* is classified as *Enterococcus faecalis*.)

The microorganism used in the present invention is selected from a group of microorganisms belonging to the genuses Enterococcus, Lactobacillus, Providencia, Fusarium, and Gibberella, and any of them which is capable of acting on threo-3-phenylserine or its halogen substitution products to produce (R)-2-amino-1-phenylethanol or its halogen substitution products, which are represented by Formula (2) can be used. In practice, they are exemplified by *Enterococcus faecalis* (NRIC 1141), *Enterococcus hirae* (IFO 3181), *Lactobacillus brevis* (NRIC 1037), *Providencia stuatii* (IFO 12930), *Fusarium anguioides* (IFO 4467), *Gibberella fujikuroi* (IFO 9977, IFO 30336, IFO 30337, IFO 31251, NRIC 1240), *Gibberella zeae* (IFO 7772), *Gibberella lateritium* (IFO 7188), *Gibberella acuminata* (IFO 30307), etc. A wild strain, mutant strain or recombinant strain induced by cell fusion or gene manipulation, of these microorganisms can preferably be used.

Microorganisms having IFO numbers are described in "List of Cultures, 9th ed. (1992)" published by The Institute for Fermentation Osaka, and can be obtained from the institute. Microorganisms having NRIC numbers are described in "Microbial Strain Catalog, 2nd ed. (1992)" published by Tokyo University of Agriculture, and can be obtained from the university.

According to the descriptions in the pages 312–320 of "List of Cultures 9th ed. (1992)" published by The Institute for Fermentation Osaka, and the pages 518–522 (Vol. 1) and the pages 1055–1059 (Vol. 2) of "Illustrated Reference Book of Fungi" written by Shunichi Udagawa et al., Kodansha (1978), the conidial generation of *Gibberella fujikuroi* is identified as *Fusarium moniliforme,* that of *Gibberella zeae* as *Fusarium graminearum* and that of *Gibberella lateritium* as *Fusarium lateritium.* Therefore, it is clear that the species indicated by the names of the complete generation of the above microorganisms are the same as those indicated by the names of their corresponding conidial generation. The use of *Fusarium moniliforme, Fusarium graminearum* or *Fusarium lateritium* is also clearly included in the scope of the present invention.

The medium used for culturing microorganisms in the present invention is not especially limited so far as the microorganisms can proliferate in the medium. As a carbon source for the above microorganisms, for example, saccharides such as glucose, fructose, sucrose, and dextrin; alcohols such as sorbitol, and glycerol; organic acids such as fumaric acid, citric acid, acetic acid, and propionic acid, and their salts; hydrocarbons such as paraffin; or mixtures of any of these chemicals can be used. As a nitrogen source, for example, ammonium salts of an inorganic acid such as ammonium chloride, ammonium sulfate and ammonium phosphate, ammonium salts of an organic acid such as ammonium fumarate and ammonium citrate, inorganic or organic chemicals containing nitrogen such as meat extract, yeast extract, corn steep liquor, casein hydrolyzates, and urea, or mixtures of any of these chemicals can be used. Nutritive sources usually used for microorganism culture such as inorganic salts, salts of essential trace metal elements, and vitamins can appropriately be added to the medium. Factors promoting the proliferation of microorganisms, amino acid sources augmenting the productivity of the objective products provided by the present invention, such as serine, tyrosine, valine, leucine, alanine, isoleucine, glycine, phenylalanine, tryptophan, threo-3-phenylserine or its halogen substitution products, vitamin $B_6$-associated factors such as pyridoxal-5'-phosphate and pyridoxal hydrochloride, or $CaCO_3$ effectively maintaining the pH of medium can be added. For example, bouillon medium is suitable for bacteria, MRS medium or GYP medium for lactic acid bacteria, and YM medium or potato-sucrose medium for molds (see pp 452–453 of "List of Cultures 9th ed. (1992)" published by The Institute for Fermentation Osaka, or pp 51–52 of "Microbial Strain Catalog, 2nd ed. (1992)" published by Tokyo University of Agriculture.).

Microorganisms are cultured in the pH range of 3.0 to 11.0, preferably 4 to 8, in the temperature range of 20° to 45° C., preferably 25° to 37° C., and under conditions appropriately selected to anaerobic or aerobic bacteria, for 5 to 120 h, preferably 24 to 96 h.

DL-threo-3-phenylserine or its halogen substitution products can easily be synthesized by a known method (for example, see K. N. F. Shaw and S. W. Fox, *J. Amer. Chem. Soc.,* 75, 3421–3424 (1953)). Literature disclosing actual synthesis of 3-(3-chlorophenyl)serine has not been known.

A substrate, a mixture of the enantiomers of threo-3-phenylserine or its halogen substitution products, which are represented by Formula (1), is added in a concentration range, wherein the substrate inhibition does not occur, at one time, at intervals, or continuously. The final concentration of the added substrate is usually 0.01 to 20% (w/w). The substrate may be added after being dissolved or dispersed in water, dissolved in an organic solvent which is not adversely affecting the reaction, or dispersed in a surfactant.

When tyrosine decarboxylase is used, its concentration for the reaction is varied depending on the concentration of a substrate, and is usually set at 0.005 to 5.0 units/mi. (One unit of the enzymatic activity is that capable of decarboxylating one $\mu$mol of a substrate at pH 5.5 at 37° C. for one min.) A commercially available enzyme, enzyme further purified from a commercially available preparation, or enzyme obtained from bacteria by a combination of known purification methods can be used. The reaction may be performed using the enzyme dispersed or dissolved in a reaction mixture, or using the enzyme can be immobilized on carrageenan gel, alginate gel, polyacrylamide gel, cellulose, agar, or the like by a known method. The enzyme reaction may be carried out in a bioreactor equipped with an ultrafiltration membrane.

When microorganisms are used, a mixture of the enantiomers of threo-3-phenylserine or its halogen substitution products can be directly added to the medium used for culturing the microorganisms. Alternatively, the microorganisms are separated by centrifugation and dispersed in a buffered solution or water, with or without post-washing. The mixture of the enantiomers of threo-3-phenylserine or its halogen substitution products is added to the dispersion. Living microorganisms as well as homogenates of the microorganisms, and acetone-treated, toluene-treated, or lyophilized cells of the microorganisms may be used. Living or treated cells of the microorganisms can be immobilized on carrageenan gel, alginate gel, polyacrylamide gel, cellulose, agar or the like by a known method to embody the present invention. The living or treated cells of the microorganisms are enabled to act in a reactor having an ultrafiltration membrane. The addition of a surfactant, such as cetylpyridinium chloride, cetyltrimethylammonium bromide, Triton X® or Tween, at a concentration of 0.001 to 0.5% may lead to an improved permeability of the substrate, the enantiomers of threo-3-phenylserine or its halogen substitution products, into the microbial body.

The following conditions are common in the uses of the microorganisms (either living or treated cells) and the enzyme:

Preventing oxygen from being in contact with the reaction mixture by replacing the gas over the reaction mixture with nitrogen, or sealing the reaction fluid by placing liquid paraffin on the top surface, may lead to a preferable result. The reaction is usually carried out in the temperature range of 5° to 70° C., preferably 20° to 40° C. for the genuses Lactobacillus and Providencia, 45° to 60° C. for the genuses Enterococcus, Gibberella and Fusarium, and 25° to 60° C. for tyrosine decarboxylase. The pH of the reaction mixture is appropriately set at a value in the range where the enzyme can decarboxylate the substrate. The pH is usually maintained at 4 to 11, preferably 5 to 9 with a buffered solution or pH-stat. The reaction can be performed under static, shaken, or stirred conditions. The solvent used for the reaction is usually water. An organic solvent such as alcohol can be added as long as its addition does not adversely affect the reaction. The produced (R)-2-amino-1-phenylethanol or its halogen substitution products can be collected and purified by a combination of conventional methods, such as ultrafiltration, concentration, column chromatography, extraction, and crystallization. The remaining optically active threo-3-phenylserine or its halogen substitution products can be collected and purified by a similar method.

DESCRIPTION OF THE PREFERRED EMBODIMENT

A preferred embodiment of the present invention will be described hereinafter, but the scope of the present invention is not only limited to the preferred embodiment. The optical purities of (R)-2-amino-1-phenylethanol or its halogen substitution products, and of optically active threo-3-phenylserine or its halogen substitution products, were measured by HPLC [column: CROWNPAK (+) (Daicel Chemical Industries, Ltd.; inner diameter: 4.6 mm, length: 150 mm, mobile phase: perchloric acid solution at pH 2.0 (pH 1.0)), flow rate: 1.0 ml/min, temperature: 10° C. (5° C.), detection: UV at 254 nm (the measurement for optically active threo-3-phenylserine or its halogen substitution products was carried out under the conditions described in the parentheses.)]. The quantitation of (R)-2-amino-1-phenylethanol or its halogen substitution products, and of optically active threo-3-phenylserine or its halogen substitution products, were carried out by reversed phase HPLC using an ODS column [column: Wakosil ODS II HG (Wako Pure Chemical Industries, Ltd.; inner diameter: 4.6 mm, length: 250 mm, mobile phase: 50 mM potassium phosphate buffered solution at pH 2.5/acetonitrile (9/1, v/v)), flow rate: 1.0 ml/min, temperature: 50° C., detection: UV at 254 nm].

The culture media used in the examples of this preferred embodiment, "Microorganism culture medium 1A", "Microorganism culture medium 1B", "Microorganism culture medium 2", "Microorganism culture medium 3", "Microorganism culture medium 4", "Microorganism culture medium 5" and "YM medium" were prepared, as follows:

Microorganism culture medium 1A: mixing 5 g of glucose, 5 g of yeast extract (Kyokuto Pharmaceutical Industrial Co., Ltd.), 5 g of polypeptone (Nihon Seiyaku Co., Ltd.), 1 g of $MgSO_4$ $7H_2O$, 0.2 g of DL-threo-3-(3-chlorophenyl)serine and 0.1 g of pyridoxal hydrochloride, bringing the total volume up to 1000 ml with deionized water, and adjusting the pH to 7.0.

Microorganism culture medium 1B: mixing 5 g of glucose, 5 g of yeast extract (Kyokuto Pharmaceutical Industrial Co., Ltd.), 5 g of polypeptone (Nihon Seiyaku Co., Ltd.), 1 g of $MgSO_4$ $7H_2O$, 0.2 g of L-tyrosine and 0.1 g of pyridoxal hydrochloride, bringing the total volume up to 1000 ml with deionized water, and adjusting the pH to 7.0.

Microorganism culture medium 2: mixing 5 g of glucose, 0.7 g of $KH_2PO_4$, 1.3 g of $(NH_4)_2PO_4$, 0.5 g of $MgSO_4$ $7H_2O$, 3 g of yeast extract (Kyokuto Pharmaceutical Industrial Co., Ltd.), 5 g of polypeptone (Nihon Seiyaku Co., Ltd.) and 0.2 g of DL-threo-3-(3-chlorophenyl)serine, bringing the total volume up to 1000 ml with deionized water, and adjusting the pH to 7.2.

Microorganism culture medium 3: mixing 20 of glycerin, 3 g of yeast extract (Kyokuto Pharmaceutical Industrial Co., Ltd.), 5 g of polypeptone (Nihon Seiyaku Co., Ltd.), 3 g of malt extract (Kyokuto Pharmaceutical Industrial Co., Ltd.), 0.1 g of pyridoxal hydrochloride and 1000 ml of deionized water, and adjusting the pH to 7.0.

Microorganism culture medium 4: mixing 5 g of glycerin, potato extract from 200 g of potato (prepared by cutting 200 g of peeled potato into 1-cm cubes, boiling them in 1000 ml of added water for 20 min, and then filtering with gauze) and 0.1 g of pyridoxal hydrochloride, bringing the total volume up to 1000 ml with deionized water, and adjusting the pH to 5.6.

Microorganism culture medium 5: mixing 24 g of glucose, 19.2 g of yeast extract (Asahi Breweries, Ltd.), 1.3 g of $KH_2PO_4$, 2.4 g of $(NH_4)_2SO_4$ $7H_2O$, 1.3 g of $MgSO_4.7H_2O$, 0.016 g of $FeSO_4$ $7H_2O$, 0.016 g of $ZnSO_4$ $7H_2O$ and 0.3 g of FS anti-foam 028 (Dow Corning Inc.), bringing the total volume up to 1000 ml with deionized water, and adjusting the pH to 6.0.

YM medium: 10 g of glucose, 3 g of yeast extract (Kyokuto Pharmaceutical Industrial Co., Ltd.), 3 g of malt extract (Kyokuto Pharmaceutical Industrial Co., Ltd.) and 5 g of polypeptone (Nihon Seiyaku Co., Ltd.), bringing the total volume up to 1000 ml with deionized water, and adjusting the pH to 6.0.

[EXAMPLE 1]

Synthesis of threo-3-(3-chlorophenyl)serine

Sodium hydroxide (80 g, 2.0 mol), glycine (100 g, 1.33 mol), and water (330 ml) were put in a 2-l separable flask, and chilled to 15° C. in a cold water bath. To this mixture was added m-chlorobenzaldehyde (375 g, 2.66 mol) at one time, and the contents were vigorously stirred. White solids were gradually appeared, and it became difficult to stir the contents after about 1 h. The reaction mixture was allowed to stand for 24 h at room temperature after stirring was halted. After chilling to 15° C., concentrated sulfuric acid (36%, 202.6 g, 2.0 mol, 176 ml) was slowly added dropwise to the reaction mixture over about 1 h. After completion of the dropwise addition, toluene (370 ml) was added to the product mixture, which was then stirred for about 1 h. The product mixture was filtered by suction, and the white solids obtained were washed with toluene (500 ml). The washed white solids were added to isopropanol (1 l), and then refluxed for 1 h. After cooling, the product mixture was filtered by suction, and then thoroughly washed with isopropanol (approximately 500 ml). The washed white solids were vacuum-dried at 50° C. for 2 days to obtain 229.4 g (yield 79.9%) of the objective chemical compound having the following properties, resulting in a yield of 79.9%.

Melting point: 169° C. (decomposed);

IR (KBr): 3094, 2896, 1634, 1600, 1574, 1479, 1434, 1401, 1338, 1200, 1055, 871, 786 and 685 $cm^{-1}$, $^1$H-NMR ($D_2$O-TMSPNa): δ 7.52 (br s, 1H), 7.45–7.38 (m, 3H), 5.30 (d, J=4.39 Hz, 1H), 3.92 (d, J=4.36 Hz, 1H);

Reference values for the erythro form $^1$H-NMR ($D_2$O-TMSPNa): δ 5.36 (d, J=4.01 Hz, 1H), 4.10 (d, J=4.09 Hz, 1H).

[EXAMPLE 2]

Microorganism culture medium 1A (30 ml) was put into each of three 100-ml Erlenmeyer flasks. After sterilization, the respective Erlenmeyer flasks were inoculated with *Enterococcus faecalis* (NRIC 1141), *Enterococcus hirae* (IFO 3181), and *Lactobacillus brevis* (NRIC 1037). By a rotary shaking cultivation method, *Enterococcus faecalis* and *Enterococcus hirae* were cultured at 37° C., and *Lactobacillus brevis* was cultured at 30° C. for 24 h. Cells were separated by centrifugation, and then suspended in 100 mM acetic acid buffered solution (pH 5.5). The optical density (OD) of the suspension at 660 nm was adjusted to 60. The adjusted suspension (1.0 ml) was put into a 21-mm inner diameter test tube. A substrate solution (1.0 ml), which contained 60 mM DL-threo-3-(3-chlorophenyl)serine/0.4 mM pyridoxal-5'-phosphate in 100 mM acetic acid buffered solution (pH 5.5), was added to the suspension. The suspension containing *Enterococcus faecalis* (NRIC 1141) or *Enterococcus hirae* (IFO 3181) was incubated with shaking at 37° C., and that containing *Lactobacillus brevis* (NRIC 1037) at 30° C. for 96 h to induce a reaction. After completion of the reaction, the supernatant was separated by centrifugation, and then the optical purity and concentration of produced 2-amino-1-(3-chlorophenyl)ethanol in the supernatant were measured by HPLC.

It was found from HPLC determination that *Enterococcus faecalis* (NRIC 1141) produced (R)-2-amino-1-(3-chlorophenyl)ethanol) at a concentration of 3.38 mM with an optical purity of 100%e.e. The yield of the reaction was 11.3% (=(3.38/(6012))×100). It was also found that *Enterococcus hirae* (IFO 3181) produced (R)-2-amino-1-(3-chlorophenyl)ethanol) at a concentration of 8.92- mM with an optical purity of 100%e.e. The yield of the reaction was 29.7% (=(8.92/(6012))×100). It was also found that *Lactobacillus brevis* (NRIC 1037) produced (R)-2-amino-1-(3-chlorophenyl)ethanol) at a concentration of 1.98 mM with an optical purity of 100%e.e. The yield of the reaction was 6.6% (=(1.98/(60/2))×100).

[EXAMPLE 3]

Cells of *Enterococcus faecalis* (NRIC 1141) and *Enterococcus hirae* (IFO 3181) were prepared, as in Example 2. The reaction was carried out under the same conditions as in Example 2, except the substrate was changed to DL-threo-3-phenylserine. The optical purity and concentration of produced 2-amino phenyl ethanol in the supernatant were measured by HPLC.

It was found from HPLC determination that *Enterococcus faecalis* (NRIC 1141) produced (R)-2-amino-1-ethanol at a concentration of 2.55 mM with an optical purity of 100%e.e. The yield of the reaction was 8.5% (=(2.55/(60/2))×100). It was also found that *Enterococcus hirae* (IFO 3181) pro- duced (R)-2-amino-1-ethanol at a concentration of 6.50 mM with an optical purity of 100%e.e. The yield of the reaction was 21.6% (=(6.50/(60/2))×100).

[EXAMPLE 4]

Microorganism culture medium 2 (10 ml) was put into a 21-mm inner diameter test tube. After sterilization, this medium was inoculated with *Providencia stuatii* (IFO 12930) (one loop), and cultured with shaking at 30° C. for 24 h. Cells were subsequently separated by centrifugation, and suspended in 100 mM $NH_4OH$—$NH_4Cl$ buffered solution (pH 8.5) (2 ml). This suspension (1.0 ml) was put into a 21-mm inner diameter test tube, and then 60 mM DL-threo-3-(3-chlorophenyl)serine/0.4 mM pyridoxal-5'-phosphate solution (1.0 ml) (solvent: 100 mM $NH_4OH$—$NH_4Cl$ buffered solution (pH 8.5)) was added. The suspension was incubated with shaking at 30° C. for 24 h. After completion of the reaction, the supernatant was separated by centrifugation. The optical purity and concentration of produced 2-amino-1-(3-chlorophenyl)ethanol in the supernatant were measured by HPLC.

It was found from HPLC determination that *Providencia stuatii* (IFO 12930) produced (R)-2-amino-1-(3-chlorophenyl)ethanol) at a concentration of 0.9 mM with an optical purity of 100%e.e. The yield of the reaction was 3.0% (=(0.9/(60/2))×100).

[EXAMPLE 5]

Microorganism culture medium 3 and Microorganism culture medium 4 (5 ml each) were put into 21-mm inner diameter test tubes respectively. After sterilization, the media were inoculated with *Gibberella fujikuroi* (IFO 30337 strain) (one loop), and then incubated with shaking at 30° C. for 48 h. Cells were subsequently separated by centrifugation, suspended in 100 mM acetic acid buffered solution (pH 5.5) (1.0 ml), and then put into 15-mm inner diameter test tubes respectively. To this suspension was added 92.8 mM DL-threo-3-(3-chlorophenyl)serine/0.4 mM pyridoxal-5'-phosphate in 100 mM acetic acid buffered solution (pH 5.5) (1.0 ml). After layering 2.0 ml of liquid paraffin on the top, the suspension was statically incubated at 30° C. for 17 h to induce a reaction. After completion of the reaction, the supernatant was separated by centrifugation. The optical purity and concentration of produced 2-amino-1-(3-chlorophenyl)ethanol in the supernatant were measured by HPLC. Results of the HPLC determination are shown in Table 1.

TABLE 1

| Medium | Optical purity (% e.e.) | Concentration (mM) | Yield (%) |
| --- | --- | --- | --- |
| Microorganism culture medium 3 | R 100 | 7.0 | 15.1 |
| Microorganism culture medium 4 | R 100 | 9.6 | 20.7 |

[EXAMPLE 6]

Cells of *Gibberella fujikuroi* (IFO 30337 strain) were prepared in Microorganism culture medium 3, as in Example 5, and statically incubated at 30° C. for 17 h under the same conditions as in Example 5 to induce a reaction, except for changing the substrate to DL-threo-3-phenylserine. After completion of the reaction, the supernatant was separated by centrifugation. The optical purity and concentration of produced 2-amino-1-phenylethanol in the supernatant were measured by HPLC. The optical purity was 100%e.e. as R form, the concentration 6.9 mM, and the yield 14.9%.

[EXAMPLE 7]

*Gibberella fujikuroi* (IFO 9977, IFO 30336, IFO 31251, NRIC 1240), *Gibberella acuminata* (IFO 30307), *Gibberella zeae* (IFO 7772), *Gibberella lateritium* (IFO 7188), and *Fusarium anguioides* (IFO 4467) were inoculated with one loop each to 5 ml of Microorganism culture medium 3, respectively. The strains of *Gibberella fujikuroi* were cultured with shaking at 30° C. for 48 h, and the other microorganisms were at 30° C. for 72 h. Cells were separated by centrifugation, and then suspended in 1.0 ml of 100 mM acetic acid buffered solution (pH 5.5). The suspensions were put into 15-mm inner diameter test tubes. To these suspensions was added 1.0 ml each of 92.8 mM DL-threo-3-(3-chlorophenyl)serine/0.4 mM pyridoxal-5'-phosphate in 100 mM acetic acid buffered solution (pH 5.5). The resulting suspension was statically incubated at 30° C. for 17 h to induce a reaction. After completion of the reaction, the supernatant was separated by centrifugation. The optical purity and concentration of produced 2-amino-1-(3-chlorophenyl)ethanol in the supernatant were measured by HPLC. Results of the HPLC determination are shown in Table 2. "R" in the column of "optical purity" indicates the R form of the product.

TABLE 2

| Strain | Optical purity (% e.e.) | Concentration (mM) | Yield (%) |
|---|---|---|---|
| Gibberella fujikuroi (IFO 9977) | R 100 | 5.1 | 11.0 |
| Gibberella fujikuroi (IFO 30336) | R 100 | 3.6 | 7.8 |
| Gibberella fujikuroi (IFO 31251) | R 100 | 0.2 | 0.4 |
| Gibberella fujikuroi (NRIC 1240) | R 100 | 0.7 | 1.5 |
| Gibberella acuminata (IFO 30307) | R 100 | 0.7 | 1.5 |
| Gibberella zeae (IFO 7772) | R 100 | 6.6 | 14.2 |
| Gibberella lateritium (IFO 7188) | R 100 | 3.4 | 7.3 |
| Fusarium anguioides (IFO 4467) | R 100 | 8.2 | 17.7 |

[EXAMPLE 8]

*Gibberella fujikuroi* (IFO 30337 strain) was cultured in 5 ml of YM medium at 30° C. for 24 h in a 21-mm inner diameter test tube with shaking. Microorganism culture medium 3 (700 ml) was placed in a 1.2-l mini jar (Marubishi Bioengineering Co., Ltd.), and sterilized at 121° C. for 15 min. After cooling, the preculture of *Gibberella fujikuroi* (1.4 ml) was inoculated to the mini jar, and cultured at 30° C. for 40.5 h (600 revolutions, 1.0 vvm). After the cultured medium (100 ml) was centrifuged, the cells were twice washed with 50 ml of 100 mM acetic acid buffered solution (pH 5.5), and suspended in 9.8 ml of the same buffered solution. To this suspension were added 0.30 g of crystalline DL-threo-3-(3-chlorophenyl)serine and 0.2 ml of 10 mM pyridoxal-5'-phosphate solution were added to the suspension, and stirred to dissolve the added substances. The resulting suspension was statically incubated at 30° C. for 39 h after layering 5 ml of liquid paraffin on the top. It was found by HPLC analysis that (R)-2-amino-1-(3-chlorophenyl)ethanol was produced at a concentration of 10.7 g/l in the reaction mixture (yield 44.8%).

[EXAMPLE 9]

Microorganism culture medium 1A (200 ml) was put into a 500-ml Erlenmeyer flask. After sterilization, it was inoculated with *Enterococcus hirae* (IFO 3181), and rotatively cultured at 37° C. for 21 h. Cells were subsequently separated by centrifugation, suspended in 100 mM acetic acid buffered solution (pH 5.5), and the optical density of the suspension at 660 nm was adjusted to 100. This cell suspension (1.96 ml) was put into a 21-mm inner diameter test tube. Crystalline DL-threo-3-(3-chlorophenyl)serine (50 mg) and 10 mM pyridoxal-5'-phosphate solution (40 μl) were added to the above suspension. This cell suspension was cultured with shaking at 37° C. for 24 h. After completion of the reaction, the optical purity and concentration of produced 2-amino-1-(3-chlorophenyl)ethanol, and those of the remaining substrate were measured by HPLC.

It was found from HPLC determination that (R)-2-amino-1-(3-chlorophenyl)ethanol was produced at a concentration of 30.7 mM with an optical purity of 100%e.e. The yield of the reaction was 26.5% (=(30.7/116.0)×100). It was also found that the optical purity and concentration of remaining (+)-threo-3-(3-chlorophenyl)serine were 100%e.e. and 57.4 mM, respectively. The percentage of the remaining (+)-threo-3-(3 -chlorophenyl)serine to the initial amount of the substrate was 49.5% (=(57.4/116)×100).

[EXAMPLE 10]

*Gibberella fujikuroi* (IFO 30337 strain) was precultured in 25 ml of YM medium at 30° C. for 24 h in a Sakaguchi flask by shaking. Microorganism culture medium 5 (600 ml) was put into a 1.2-l mini jar (Marubishi Bioengineering Co., Ltd.), and sterilized at 121° C. for 15 min. After cooling, the mini jar was inoculated with 12 ml of the preculture, and cultured at 30° C. for 72 h (900 revolutions, 1.0 vvm). The cultured medium (300 ml) was taken out, and then centrifuged. The cells were twice washed with the same amount of deionized water as of the culture medium used, suspended in deionized water, and the volume of the suspension was adjusted to 60 ml. In a 1.2-l mini jar (Marubishi Bioengineering Co., Ltd.) were placed deionized water (430 ml), crystalline DL-threo-3-(3-chlorophenyl)serine (16.7 g), and 10 ml of 10 mM pyridoxal-5'-phosphate solution, and stirred to make a complete solution. The cell suspension (60 ml) was added to the above substrate mixture. The reaction mixture was incubated at 50° C. for 42 h (200 revolutions) with a slight bubbling of nitrogen gas. The pH of the reaction mixture was maintained at 6.2 throughout the reaction by adding 10% $H_2SO_4$. After completion of the reaction, the reaction mixture was analyzed by HPLC. It was found that (R)-2-amino-1-(3-chlorophenyl)ethanol was produced at a concentration of 15.2 g/l in the reaction mixture (yield 44.8%). It was also found that (+)-threo-3-(3-chlorophenyl)serine remained at a concentration of 19.6 g/l, and the percentage of the remaining (+)-threo-3-(3-chlorophenyl)serine to the initial amount of the substrate was 49.9% (=19.6×0.425/16.7×100). The weight of the resulting liquid fraction was 425 g.

[EXAMPLE 11]

Purification of (+)-threo-3-(3-chlorophenyl)serine

Deionized water (100 ml) was added to 100 ml of the reaction mixture in Example 10 after completion of the reaction. The diluted reaction fluid was warmed to 50° C., stirred, and then cells were removed by centrifugation. Macromolecular materials, such as proteins, in the supernatant were removed by passing through an ultrafiltration membrane (Amicon Inc). The filtered supernatant was concentrated in an evaporator in vacuo to reduce the weight of the supernatant to about 23 g. The concentrated supernatant was stored overnight at 4° C. Crude crystals were separated by filtration, and washed with 10 g of chilled pure water. The obtained crude crystals were added to 15 g of pure water, and dissolved by warming at 90° C. under stirred conditions. The resulting warmed solution was filtered. 2-Propanol (15 g) was quickly added to the filtered solution, which was then stored overnight at 4° C. Crystals were separated by filtration, washed with a mixture of water and 2-propanol (1/1) and vacuum-dried to obtain white crystals (0.76 g) and having the following properties. The yield of the purification was 39%.

Chemical purity: 99.5%, $[\alpha]^{25}_D$+15.0° (c 0.215, $H_2O$);

Optical purity (analyzed using CROWNPAK CR(+)) of (+)-threo-3-(3-chlorophenyl)serine: 100%e.e.;

$^1$H-NMR ($D_2O$-TMSPNa): δ 7.52 (br s, 1H), 7.45–7.38 (m, 3H), 5.30 (d, J=4.38 Hz, 1H), 3.92 (d, J=4.38 Hz, 1H).

[EXAMPLE 12]

Tyrosine decarboxylase (0.1 U) (Sigma, product code No.: T-4379; activity: 0.07 U/mg, derived from *Streptococcus faecalis* according to the catalogue provided) was mixed in a 15-mm inner diameter test tube with DL-threo-3-(3-chlorophenyl)serine and pyridoxal-5'-phosphate, so that the final concentration in the mixture was adjusted to 30 mM for the former, 0.2 mM for the latter at a total volume of 1.0 ml. The mixture was statically incubated at 30° C. for 21 h. After completion of the reaction, the mixture was filtered with an ultrafiltration membrane having 0.22 μm pores. The filtered mixture was appropriately diluted to obtain samples for HPLC analysis. It was found by HPLC determination that (R)-2-amino-1-(3-chlorophenyl)ethanol was produced at a concentration of 4.7 mM in the mixture, and its optical purity was 100%e.e. The yield of the reaction was 15.7% (=4.7/(60/2)×100).

[EXAMPLE 13]

The same steps were performed as in Example 12, except for further purifying tyrosine decarboxylase. The purification of tyrosine decarboxylase was carried out by a method described by S. Allenmark et al. in *J. Chromatography*, 153, 239–245 (1978).

Tyrosine decarboxylase charged on phenylsepharose 4B (Pharmacia) in a column was eluted with 1.0M sodium acetate buffered solution (pH 6.0). Active fractions belonging to a single peak were collected, dialyzed against 0.1M sodium acetate buffered solution (pH 5.5), and concentrated with an ultrafiltration membrane to be used for the reaction. Determination results obtained by HPLC analysis of a reaction mixture were almost the same as in Example 12.

[EXAMPLE 14]

The same steps were performed as in Example 12, except that tyrosine decarboxylase purified from a homogenate of *Enterococcus faecalis* (NRIC 1141) cells. The purification of tyrosine decarboxylase from a homogenate of *Enterococcus faecalis* (NRIC 1141) cells was carried out as follows:

*Enterococcus faecalis* (NRIC 1141) (one loop) was inoculated into sterilized Microorganism culture medium 1A, and cultured under rotation at 37° C. for 24 h. Cells were separated by centrifugation. Approximately 1 g of cells (wet mass) was suspended in 2.5 ml of 0.1M acetic acid buffered solution (pH 5.5), and sonicated. The supernatant was separated by centrifugation, and treated with 2% protamine sulfate to remove nucleic acids. The treated supernatant was thoroughly dialyzed against 1.0M acetic acid buffered solution (pH 6.0), loaded onto a column of phenylsepharose 4B equilibrated with 1.0M acetic acid buffered solution (pH 6.0), and eluted with the same buffered solution. Active fractions belonging to a single peak were collected, dialyzed against 0.1M sodium acetate buffered solution (pH 5.5), and concentrated with an ultrafiltration membrane to be used for the reaction. Determination results obtained by HPLC analysis of the reaction mixture were almost the same as in Example 12.

[EXAMPLE 15]

The same steps were performed as in Example 12, except for using tyrosine decarboxylase purified from a homogenate of *Enterococcus hirae* (IFO 3181) cells.

The purification of tyrosine carboxylase from a homogenate of *Enterococcus hirae* (IFO 3181) cells was carried out in such a similar manner as that for *Enterococcus faecalis* (NRIC 1141) cells in Example 14. It was found by HPLC determination that (R)-2-amino-1-(3-chlorophenyl)ethanol was produced at a concentration of 10.6 mM, and its optical purity was 100%e.e. The yield of the reaction was 35.3% ( 10.6/(60/2)×100).

[EXAMPLE 16]

Tyrosine decarboxylase (0.030 U) prepared from cells of *Enterococcus hirae* (IFO 3181) in Example 15 was mixed in a 15-mm inner diameter test tube with DL-threo-3-(3-chlorophenyl)serine and pyridoxal-5'-phosphate, so that the final concentration in the mixture was adjusted to 35 mM for the former, 0.2 mM for the latter in a total volume of 1.0 ml. The reaction was performed by statically incubating the mixture at 37° C. for 48 h. It was found by HPLC determination that (R)-2-amino-1-(3-chlorophenyl)ethanol was produced at a concentration of 17.6 mM in the mixture, and its optical purity was 100%e.e. The yield of the reaction was 50.3% (=17.6/35×100). It was also found that (+)-threo-3-(3-chlorophenyl)serine remained at a concentration of 17.7 mM, and its optical purity was 100%e.e. The percentage of the remaining (+)-threo-3-(3-chlorophenyl)serine to the initial amount of the substrate was 50.6% (=(17.7/35)×100).

ADVANTAGES OF THE INVENTION

According to the present invention, a mixture of the enantiomers of threo-3-phenylserine or its halogen substitution products, which are represented by Formula (1), can be stereoselectively decarboxylated by using tyrosine decarboxylase, or microorganisms of the genuses Enterococcus, Lactobacillus, Providencia, Fusarium, and Gibberella. Consequently, almost optically pure (R)-2-amino-1-phenylethanol or its halogen substitution products, which are represented by Formula (2), can be economically produced on an industrial scale. At the same time, one of the enantiomers of threo-3-phenylserine or its halogen substitution products can be selectively left, and optically active threo-3-phenylserine or its halogen substitution products can be economically obtained on an industrial scale.

Formula (1)
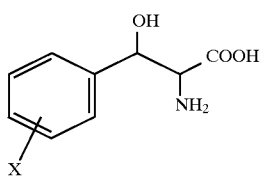

Formula (2)
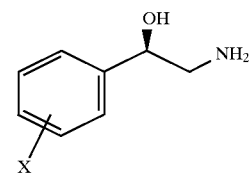

X is H, F, Cl, Br, or I, and may be located at any of the ortho, meta, and para positions.

We claim:

1. An optically active (+)-threo form of 3-(3-chlorophenyl)serine.

2. The optically active 3-(3-chlorophenyl)serine of claim 1, wherein the optical purity of said 3-(3-chlorophenyl)serine is about 99% e.e.

3. The optically active 3-(3-chlorophenyl)serine of claim 1, wherein the optical purity of said 3-(3-chlorophenyl)serine is about 100% e.e.

* * * * *